(12) United States Patent
Qin et al.

(10) Patent No.: US 10,394,828 B1
(45) Date of Patent: Aug. 27, 2019

(54) METHODS, SYSTEMS AND COMPUTER READABLE STORAGE MEDIA FOR GENERATING QUANTIFIABLE GENOMIC INFORMATION AND RESULTS

(71) Applicant: EMORY UNIVERSITY, Atlanta, GA (US)

(72) Inventors: Zhaohui Qin, Atlanta, GA (US); Fusheng Wang, Tucker, GA (US); William Stephen Pittard, Atlanta, GA (US)

(73) Assignee: Emory University, Atlanta, GA (US)

( * ) Notice: Subject to any disclaimer, the term of this patent is extended or adjusted under 35 U.S.C. 154(b) by 605 days.

(21) Appl. No.: 14/696,714

(22) Filed: Apr. 27, 2015

Related U.S. Application Data

(60) Provisional application No. 61/984,194, filed on Apr. 25, 2014.

(51) Int. Cl.
*G06F 17/30* (2006.01)
*G06F 16/2457* (2019.01)
*G16B 50/00* (2019.01)

(52) U.S. Cl.
CPC ....... *G06F 16/24578* (2019.01); *G16B 50/00* (2019.02)

(58) Field of Classification Search
CPC ............ G06F 17/3053; G06F 16/24578
USPC ........... 707/723; 536/24.5; 435/6.13; 705/3; 702/20; 506/9
See application file for complete search history.

(56) References Cited

U.S. PATENT DOCUMENTS

| | | | |
|---|---|---|---|
| 8,148,067 B2 * | 4/2012 | Lal | C12Q 1/6809 435/6.1 |
| 8,163,896 B1 * | 4/2012 | Bentwich | C07K 14/4702 435/320.1 |
| 8,165,414 B1 | 4/2012 | Yagnik | |
| 8,207,316 B1 * | 6/2012 | Bentwich | C07K 14/005 536/23.1 |

(Continued)

FOREIGN PATENT DOCUMENTS

| | | |
|---|---|---|
| WO | 2007145789 A2 | 12/2007 |
| WO | 2013044354 A1 | 4/2013 |

OTHER PUBLICATIONS

Marguerat, Samuel et al., "RNA-seq: from technology to biology," Cell. Mol. Life Sci, 2010. (Year: 2010).*

(Continued)

*Primary Examiner* — Alexandria Y Bromell
(74) *Attorney, Agent, or Firm* — Emory Patent Group

(57) ABSTRACT

Methods, systems and computer-readable storage media relate to generating quantitative genomic information. The methods may include processing at least one dataset obtained from a data repository, the at least one dataset including raw genomic data and descriptive data. The descriptive data may include experiment data. The methods may also include determining quantitative information for each group of one or more genes of the at least one dataset based on experiment data and/or at least one coordinate system. The quantitative information may correspond to one or more quantitative measures of one or more biological properties associated with a processed genomic dataset. The quantitative information can provide a normalized value that can be compared across different experiment types and thus can provide biological knowledge and insights.

18 Claims, 11 Drawing Sheets

(56) References Cited

U.S. PATENT DOCUMENTS

| | | | |
|---|---|---|---|
| 8,275,737 B2 | 9/2012 | Kupershmidt et al. | |
| 8,364,665 B2 | 1/2013 | Su et al. | |
| 2003/0181876 A1* | 9/2003 | Ahn | A61B 17/221 |
| | | | 604/267 |
| 2003/0181987 A1* | 9/2003 | Muirhead-Allwood | |
| | | | A61F 2/32 |
| | | | 623/22.15 |
| 2003/0220820 A1* | 11/2003 | Sears | G06Q 50/24 |
| | | | 705/3 |
| 2003/0233218 A1* | 12/2003 | Schilling | G16B 5/00 |
| | | | 703/11 |
| 2003/0233365 A1 | 12/2003 | Schmit et al. | |
| 2004/0234995 A1* | 11/2004 | Musick | G16B 50/00 |
| | | | 435/6.13 |
| 2006/0185027 A1* | 8/2006 | Bartel | C12N 15/111 |
| | | | 800/14 |
| 2007/0031890 A1* | 2/2007 | Wohlgemuth | C12Q 1/6881 |
| | | | 435/7.1 |
| 2007/0111933 A1* | 5/2007 | Kopchick | A61K 38/1709 |
| | | | 435/6.1 |
| 2007/0178473 A1* | 8/2007 | Chen | G16B 35/00 |
| | | | 435/6.11 |
| 2008/0281818 A1* | 11/2008 | Tenenbaum | G16B 40/00 |
| | | | 707/707 |
| 2009/0222400 A1 | 9/2009 | Kupershmidt et al. | |
| 2010/0151467 A1* | 6/2010 | Wohlgemuth | C12Q 1/6881 |
| | | | 435/6.1 |
| 2010/0318528 A1 | 12/2010 | Kupershmidt et al. | |
| 2011/0314367 A1 | 12/2011 | Chang et al. | |
| 2012/0172238 A1* | 7/2012 | Varadan | C12Q 1/6813 |
| | | | 506/2 |
| 2012/0322675 A1* | 12/2012 | Gilbert | C12Q 1/6809 |
| | | | 506/9 |
| 2013/0088942 A1* | 4/2013 | Perko | G04R 60/10 |
| | | | 368/278 |
| 2013/0110407 A1 | 5/2013 | Baccash et al. | |
| 2013/0226859 A1 | 8/2013 | Hatami-Hanza | |
| 2013/0245958 A1* | 9/2013 | Forster | G16B 30/00 |
| | | | 702/19 |
| 2013/0246319 A1 | 9/2013 | Tamayo et al. | |
| 2013/0289890 A1 | 10/2013 | Haiminen et al. | |
| 2013/0289891 A1 | 10/2013 | Haiminen et al. | |
| 2013/0296183 A1* | 11/2013 | Eggan | C12Q 1/6881 |
| | | | 506/9 |
| 2014/0038986 A1* | 2/2014 | Gaulis | C07D 401/12 |
| | | | 514/253.05 |
| 2014/0088942 A1* | 3/2014 | Li | G06F 19/12 |
| | | | 703/11 |

OTHER PUBLICATIONS

Nagarajan, Niranjan et al., "Sequence assembly demystified," Nature Reviews, Macmillan Publishers, 2013. (Year: 2013).*

Adler et al. "Mining for coexpression across hundreds of datasets using novel rank aggregation and visualization methods." Genome Biology, 2009; 10:R139.

Anders et al. "Differential expression of RNA-Seq data at the gene level—the DESeq package," DESeq version 1.15.3, 2013; [retrieved from the Internet <URL:dmrocke.ucdavis.edu/Class/BST226.2014.Winter/DESeq%20Pkg.pdf> on Feb. 23, 2018].

Bassani et al. "R and Bioconductor for the Analysis of Massive Genomic Data" presentation. 2nd MilanoR meeting, Sep. 2012; [retrieved from the Internet <URL:http://www.milanor.net/blog/wp-content/uploads/2012/09/milanoR.201209.04_bioconductor.bassani.pdf> on Feb. 23, 2018].

Boogaerts et al. "Visualizing High Dimensional Datasets Using Parallel Coordinates: Application to Gene Prioritization." Proceedings of the 2012 IEEE 12th International Conference on Bioinformatics & Bioengineering (BIBE), Larnaca Cyprus, 2012: pp. 52-57.

Ferandez-Suarez et al. "Advanced Genomic Data Mining." PLOS Computational Biology, 2008; 4(9): e1000121.

Gerstein, Mark. "Integrative database analysis in structural genomics." Nature Structural Biology, Structural Genomics Supplement, 2000: (7):960-963.

Johnson et al. "An Open Access Database of Genome-wide Association Results." BMC Medical Genetics, 2009; 10:6.

Kolde et al. "Robust rank aggregation for gene list integration and meta-analysis." Bioinformatics, 2012; 28(4):573-580.

Morrison et al. "GeneRank: Using Search Engine Technology for the Analysis of Microarray Experiments." BMC Bioinformatics, 2005; 6:233.

Nagarajan et al. "Microarray Meta-Miner (MMM): an integrated method and a web tool to identify genes with similar expression profile." 2012 2nd International Conference on Computer Technology and Development (ICCTD 2010), 2010; pp. 70-74.

Nigam et al. "Rat Genome Database: a unique resource for rat, human, and mouse quantitative trait locus data." Physiological Genomics, 2013; 45:809-816.

Pepke et al. "Computational for ChIP-seq and RNA-seq studies." Nature Methods Supplement, 2009; 6(11):S22-S32.

Pers et al. "MetaRanker 2.0: a web server for prioritization of genetic variation data." Nucleic Acids Research, 2013; 41:W104-108.

Scheffer et al. "Data Mining and Text Mining for Bioinformatics: Proceedings of the European Workshop." Held in Conjunction with ECML/PKDD, Dubrovnik Croatia, 2003: pp. 1-75; [retrieved from the Internet <URL:http://citeseerx.ist.psu.edu/viewdoc/download?doi=10.1.1.385.8184&rep=rep1&type=pdf> on Feb. 23, 2018].

Singh et al. "High Sensitivity Data Mining from Biological Databases: Non-Homology Based Sequence Retrieval." [retrieved from the Internet <URL:https://www.researchgate.net/publication/252465398_High_Sensitivity_Data_Mining_from_Biological_Databases_Non-Homology_Based_Sequence_Retrieval> on Feb. 23, 2018].

Wang et al. "Gene set enrichment analysis of RNA-Seq data: integrating differential expression and splicing." BMC Bioinformatics, 2013; 14(Suppl 5):S16.

Wu et al. "A preconditioned conjugate gradient algorithm for GeneRank with application to microarray data mining." Data Mining and Knowledge Discovery, 2013: 26:27-56.

* cited by examiner

METHODS, SYSTEMS AND COMPUTER READABLE STORAGE MEDIA FOR GENERATING QUANTIFIABLE GENOMIC INFORMATION AND RESULTS

CROSS REFERENCE TO RELATED APPLICATION

This application claims priority to Provisional Application Ser. No. 61/984,194 filed Apr. 25, 2014, which is hereby incorporated by reference in its entirety.

BACKGROUND

Continuous and rapid advances in high-throughput technologies have resulted in exponential growth of genomics data. These rich genome-wide datasets can offer new and exciting opportunities to increasing an understanding all aspects of biological systems. However, currently, there are not ways to effectively utilize and analyze the massive genomics data resource.

SUMMARY

Thus, there is a need for analyzing genome-wide profiling datasets as a whole.

The disclosure relates to systems, methods, and computer-readable media storing instructions and/or a data structure for generating quantifiable genomic information. The disclosure also relates to systems, methods, and computer-readable media storing instructions for generating a ranking of the genomic information based on a query.

In some embodiments, the methods relate to a method of generating comparable genomic information from a plurality of raw genomic datasets. The method may include processing at least one dataset obtained from a data repository. The at least one dataset may include raw genomic data and descriptive data. The descriptive data may include experiment data. The method may also include determining quantitative information for each group of one or more genes of the at least one dataset based on experiment data and/or one or more coordinate systems. The quantitative information may correspond to one or more quantitative measures of one or more biological properties associated with a processed genomic dataset. The method is computer-implemented.

In some embodiments, the methods may relate to a method of ranking of genomic information based on a query for genomic information. The method may include processing a query for genomic information. The query may correspond to a query for a single gene, a query for a set of two or more genes, and/or query for a genomic region of one or more genes. The method may further include selecting a quantitative database from a plurality of different quantitative databases based on the query. Each quantitative database may include quantitative information with respect to a genomic coordinate system. The method may also include retrieving the quantitative information associated with the genomic information from the selected quantitative database based on the query. The quantitative information may correspond to one or more quantitative measures of one or more biological properties associated with one or more processed genomic datasets obtained from a data repository. The method may further include processing the quantitative information to determine a ranking of the genomic information based on the quantitative information; and generating results. The results may include the ranking of the genomic information based on the quantitative information; the genomic information including genomic data and descriptive data. In some embodiments, method may further include outputting the results. The method is computer-implemented.

In some embodiments, the systems may relate to a system for generating comparable genomic information from a plurality of raw genomic datasets. The system may include at least one processor; and a memory. In some embodiments, the processor may be configured to cause processing at least one dataset obtained from a data repository. The at least one dataset may include raw genomic data and descriptive data and the descriptive data may include experiment data. The processor may be configured to further cause determining quantitative information for each group of one or more genes of the at least one dataset based on experiment data and/or one or more coordinate systems. The quantitative information may correspond to one or more quantitative measures of one or more biological properties associated with a processed genomic dataset.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1A:
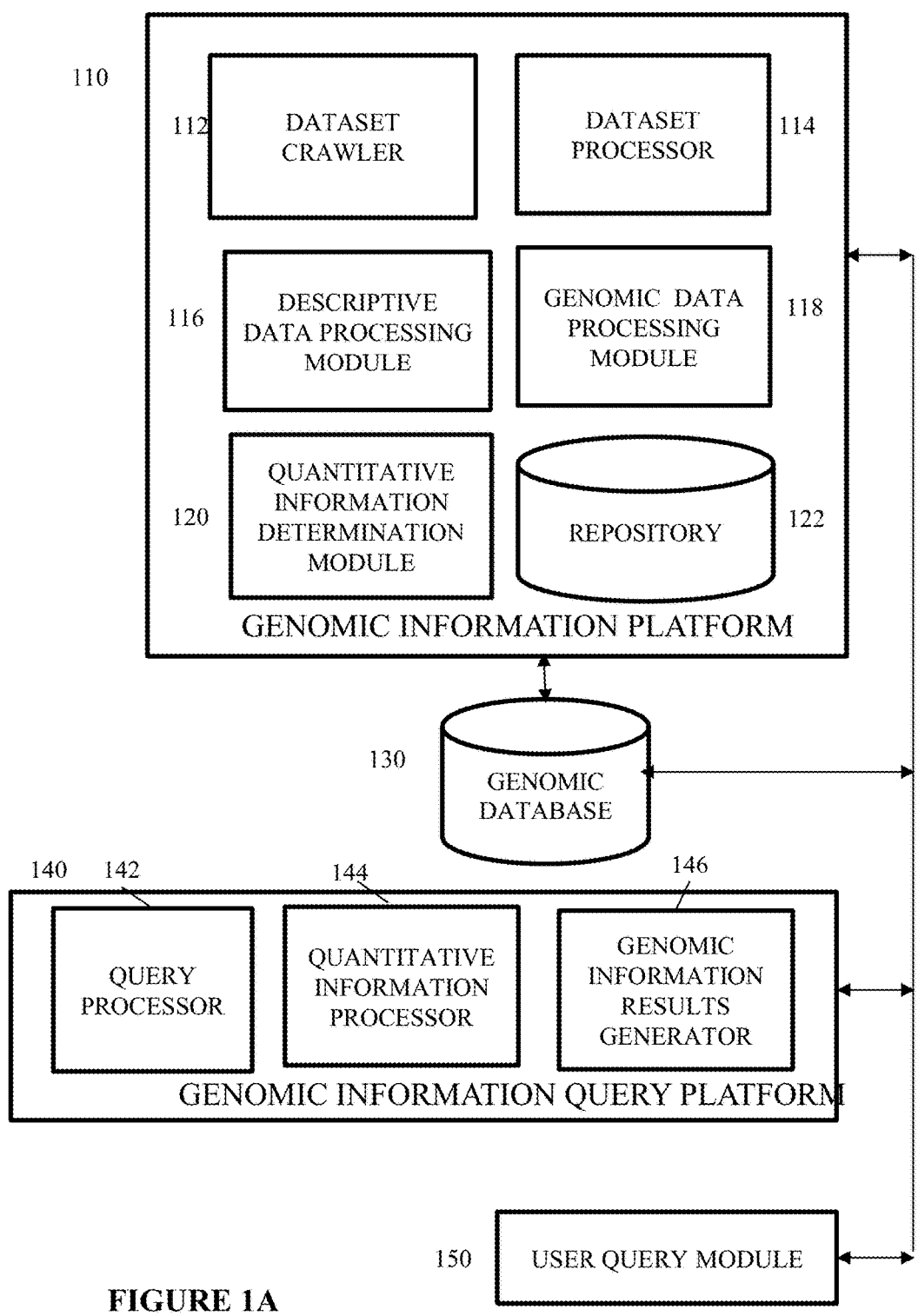
FIG. 1A shows a block diagram illustrating a system according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed methods, systems, and computer-readable media relate to a system capable of processing raw genomic data to generate genomic information that can be comparable across different data types. The system can provide a framework on how to utilize and analyze available genomics data that has been generated. The system can process raw genomics data into genomic information having quantitative measure(s) that can provide biological knowledge and insights. In this way, the massive genomics data resource may be more efficiently and effectively utilized.

FIG. 1A shows an example of a system 100 capable of generating genomic information for storage in a database from a plurality of datasets and processing a query to generate results from the database according to embodiments.

As shown in FIG. 1, the system 100 may include a genomic information platform 110 configured to generate genomic information from a plurality of processed datasets. Genomic information for each dataset may include processed genomic data and descriptive data. In some embodiments, the genomic information may include quantitative information associated with the dataset. The quantitative information may relate to one or more quantitative measures of one or more biological properties. In some embodiments, the biological properties may include but are not limited to protein-DNA interaction (ChIP-seq), strength gene expression (RNA-seq), DNA methylation (BS-seq), nucleosome position (MNase-seq), among others, or a combination thereof. In some embodiments, the quantitative information may be determined for a group of one or more genes in each track (processed data). The quantitative information may be based on a genomic coordinate system (or space) and/or experiment information. In some embodiments, the coordinate systems may include but are not limited to gene-based coordinate system, genomic region-based coordinate system, exon-based coordinate system, miRNA-based coordinate system, single nucleotide polymorphism-based coordinate system, among others, or a combination thereof. In this way, the quantitative information can provide normalized or reference value(s) for which the genomic information can be comparable across different data types.

In some embodiments, the genomic information may be stored in a genomic information database 130. In some embodiments, the database 130 may be any type of data structure, such as relational, hierarchal, object-oriented and/or or the like. In some embodiments, the database may be a relational database that includes a plurality of separate data structures, such as tables, configured to store the information. In other embodiments, the database 130 may include a plurality of databases for the information. In some embodiments, the database 130 may include separate databases and/or tables for each coordinate system for the processed genomic data and the descriptive data.

Figure 1B:
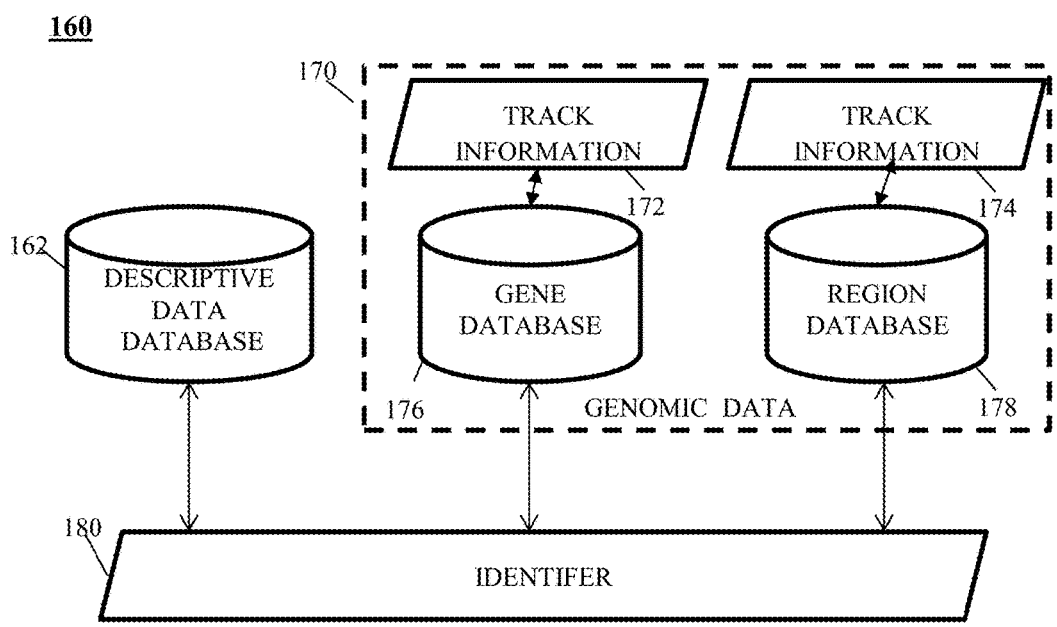
FIG. 1B shows a block diagram illustrating the genomic database according to embodiments.

FIG. 1B shows an example of the structure of a genomic information database 160 according to embodiments. In some embodiments, the database 130 may have the same structure as genomic information database 160 shown in FIG. 1B. In other embodiments, the database 130 may have a different structure.

As shown in FIG. 1B, the genomic database 160 may include a descriptive database 162 and a genomic database 170. The genomic data database 170 may include a gene-based database 174 and a region-based database 178. It will be understood that the genomic information database 160 may include a plurality of tables instead of separate databases. The genomic database 170 (e.g., the gene-based database 174 and the region-based database 178) may be associated with the descriptive data database 162 by an identifier 180. The identifier 180 may include a number, an alphabetical character(s), among others, or a combination thereof.

In some embodiments, the genomic data database 170 may include a plurality of stored track information. The track information may correspond to processed genomic data from a dataset according to embodiments. For each dataset, the track information from a processed genomic dataset may be stored with respect to one or more genomic coordinate systems. The genomic coordinate systems may include a gene coordinate system and/or a genomic region coordinate system. For example, track information 172 may be stored with respect to individual genes in a gene coordinate system in the gene-based database 176 and track information 174 may be stored with respect a group of one or more genes in the region coordinate system in the region-based database 178. The group of one or more regions may define each region in the region coordinate system.

In some embodiments, the genomic information platform 110 may include a database crawler 112. The database crawler 112 may be configured to automatically detect and collect new data from genomics data deposited in repositories. For example, the repositories may be public (such as, GEO, ArrarExpress, SRA, among others) and/or private repositories. In some embodiments, the dataset crawler may download the genomic dataset(s) and store them temporarily in a data repository 122 (e.g., any temporary memory) for processing by a dataset processor 114. In some embodiments, the dataset crawler 112 may automatically access depositories to determine new datasets based on a schedule. For example, for each scheduled period, the crawler may be configured to read a list of source databases to be accessed for new datasets. The list of source databases may be any public or private depositories. The list may be compiled, for example, by the user and/or manager of the database. In some embodiments, the crawler 112 may be configured to read the descriptive information into the genomic database 130 and identify the latest timestamp of datasets in each source database listed. The crawler 112 may be configured to download any dataset in each source database that was deposited since the last timestamp. The crawler 112 may then store the data in the data repository 122.

In some embodiments, the dataset processor 114 may be configured to extract the descriptive data and the genomic data from each dataset obtained by the database crawler 112.

In some embodiments, the genomic information platform 110 may include a descriptive data processing module 116. The descriptive data processing module 116 may be configured to process the descriptive data and/or store the descriptive data in association with the genomic data. The descriptive data may be processed to determine experiment information, such as experiment type.

In some embodiments, the genomic information platform 110 may include a genomic data processing module 118. The genomic data processing module 118 may be configured to process the raw genomic data by mapping the genomic data to a reference genome.

In some embodiments, the genomic information platform 110 may include a quantitative information determination module 120. The quantitative information determination module 120 may be configured to determine quantitative information from the processed genomic data for each dataset. In some embodiments, the quantitative information may relate to one or more quantitative measures of one or more biological properties. In some embodiments, the biological properties may include but are limited to protein-DNA interaction (ChIP-seq), strength gene expression (RNA-seq), DNA methylation (BS-seq), nucleosome position (MNase-seq), among others, or a combination thereof. In some embodiments, the quantitative information may be determined for a group of one or more genes for each track in each dataset. The quantitative information may be based on the genomic coordinate system (or space) and/or experiment information.

In some embodiments, the system 100 may include a genomic information query platform 140 configured to process a user query and generate genomic information results from the genomic database 130 from a user query. In some embodiments, the platform 140 may include a query processor 142 configured to process a user query. The query processor 142 may be configured to process a user query to determine the type of query. The type of query may include but is not limited to a single gene query, a gene set query, genomic region query, among others, or a combination thereof.

In some embodiments, the platform 140 may include a quantitative information processor 144. The quantitative information processor 144 may process the quantitative information associated with the gene(s) and/or region(s) corresponding to the query. The quantitative information processor 144 may be configured to determine the potential relevance of the genomic information to the query by ranking the genomic information associated with the query based on the quantitative information.

In some embodiments, the platform 140 may include a genomic information results generator 146. The genomic information results generator 146 may be configured to compile the results (the genomic information and associated descriptive data) based on the rank of the quantitative information. In some embodiments, the genomic information results generator 146 may include related links to the raw genomic dataset and/or descriptive data associated with the genomic data.

In some embodiments, the system may include a user query module 150. The user query module 150 may be a user interface configured to query the genomic database 130. The user interface query module 150 may be configured to communicate with the genomic database 130 via the genomic information query platform 140.

In some embodiments, the system 100 may include a different set of systems or modules, including additional systems or modules, including fewer systems or modules, or sets in which the functionality of the systems or modules is divided or consolidated.

In some embodiments, the modules and/or systems of the system 100 may be connected to a data network, a wireless network, or any combination thereof. In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture.

Figure 2:
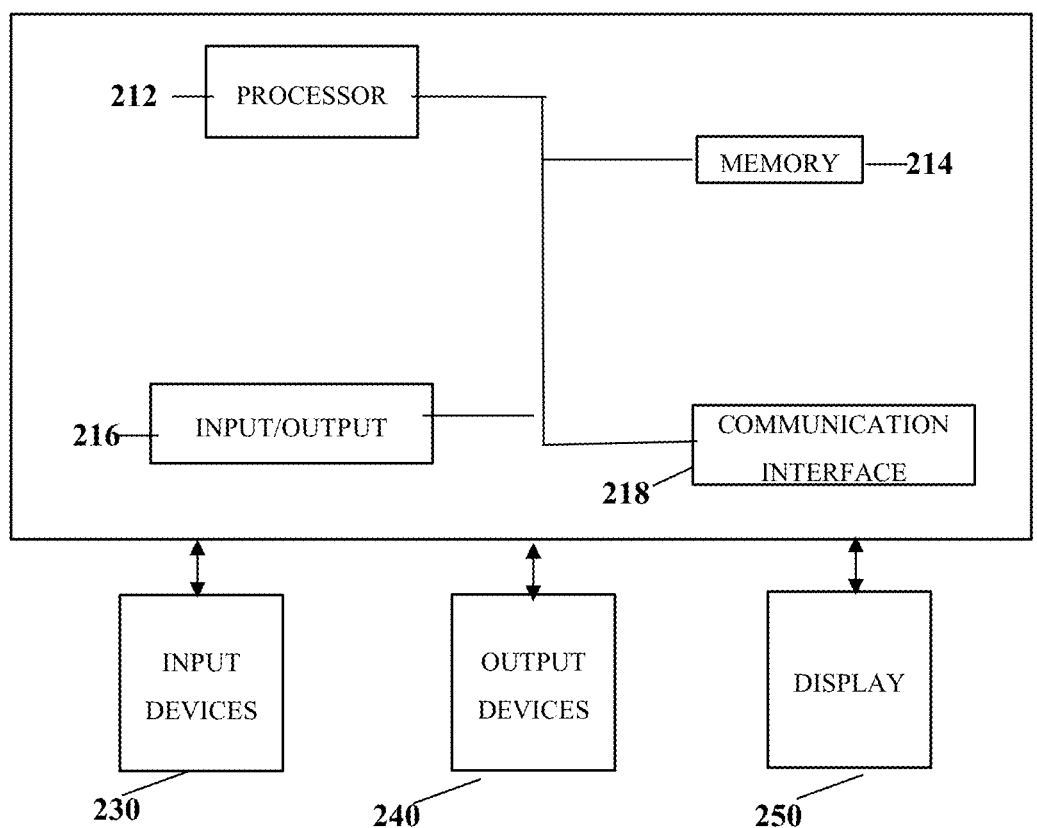
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The CPU 212 may be coupled directly or indirectly to one or more computer—readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

The CPU 212 may be configured to determine individualized treatment margins. In some embodiments, the CPU 212 may be capable of performing the data processing and/or generation of treatment plan. In other embodiments, the system may include a separate CPU for performing the data processing and/or generation of treatment plan.

In some embodiments, another computer system may assume the data analysis or other functions of the CPU 212. In response to commands received from the input device, the programs or data stored in the memory 214 may be archived in long term storage or may be further processed by the processor and presented on a display.

In some embodiments, the system 210 may include a communication interface 218 configured to conduct receiving and transmitting of data between other modules on the system and/or network. The communication interface 218 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 216 configured for receiving information from one or more input devices 230 (e.g., a keyboard, a mouse, and the like) and/or conveying information to one or more output devices 240 (e.g., a printer, a CD writer, a DVD writer, portable flash memory, etc.). In some embodiments, the one or more input devices 230 may configured to control, for example, the generation of the margins and/or treatment plan, display of the margins and/or treatment plan on a display 250, printing of the margins and/or treatment plan by a printer interface, among other things.

Figure 3A:
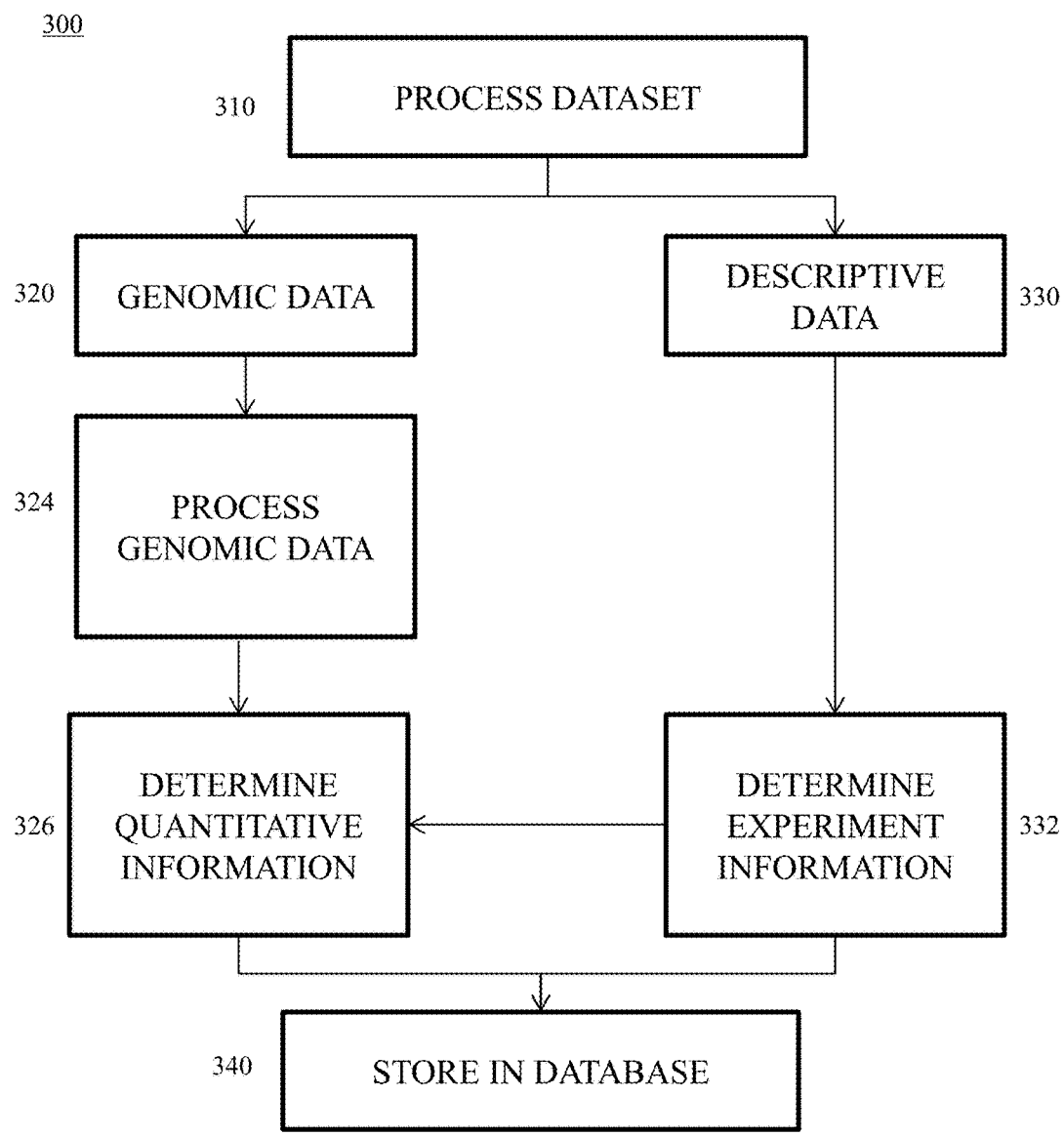
FIG. 3A shows a method of processing a dataset to generate genomic information for storage in a database according to embodiments.

FIG. 3A illustrates a method 300 for generating genomic information for storage in the database 130 according to embodiments. The system for carrying out the embodiments of the methods disclosed herein (FIGS. 3-9) is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel.

Unless stated otherwise as apparent from the following discussion, it will be appreciated that terms such as "mapping," "averaging," "combining," "comparing," "generating," "determining," "obtaining," "processing," "computing," "selecting," "receiving," "summing," "estimating," "calculating," "quantifying," "outputting," "acquiring," "analyzing," "approximating," "continuing," "resuming," "using," "retrieving," "sorting," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

As shown in FIG. 3A, the method 300 may include a step 310 of processing a dataset, for example, stored in the data repository 122 by the dataset crawler 112. In some embodiments, the step 310 may include processing the dataset to extract the genomic data 320 and descriptive data 330, for example, by the dataset processor 114.

In some embodiments, the genomic data 320 may include genetic sequence data. In some embodiments, the genetic sequence data may be raw sequencing read data. The raw sequencing read data may include but is not limited to sequencing read data in the fastq format generated from a sequencing platform. In some embodiments, the sequencing platform may be any Next Generation Sequencing (NGS) platform, such as Ion Torrent's PGM, Pacific Biosciences' RS and the Illumina MiSeq.

In some embodiments, the method 300 may include a step 324 of processing the raw genomic data by processing each read so that it is mapped to a location on a reference genome.

Figure 3B:
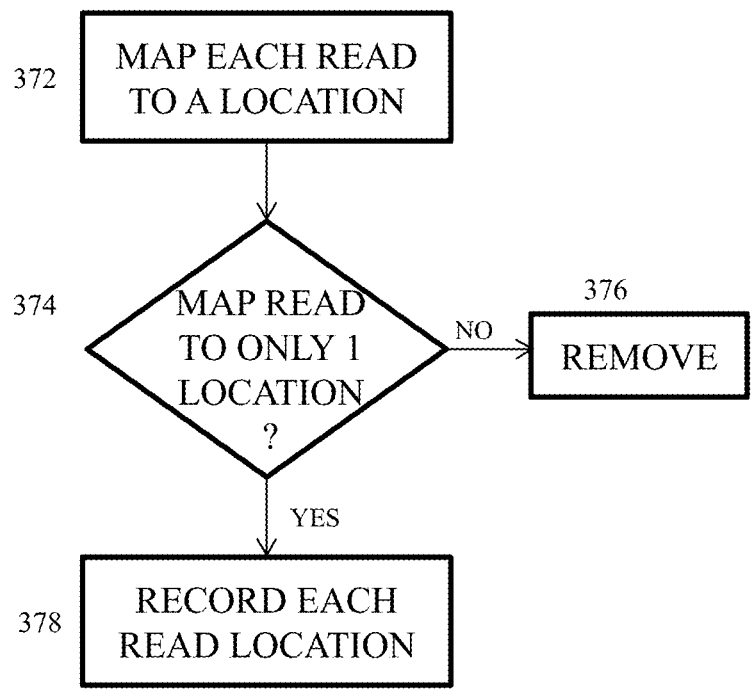
FIG. 3B shows a method of processing genomic data according to embodiments.

FIG. 3B shows a method 370 of processing the raw genomic data according to embodiments, for example, by the genomic data processing module 118. In some embodiments, other methods may be used.

In some embodiments, the method 370 may include a step 372 of mapping each read to a reference genome. In some embodiments, the reference genome may be any version of NCBI reference genome and may be updated to correspond to the most recent version of the genome. Next, after step 372, the method 370 may include a step 374 of determining whether a read is mapped to more than one location. If the read is mapped to more than one location (NO at step 376), then that read(s) are removed (step 376). Next, only reads that are uniquely mapped to the reference genome are retained and their mapped positions are recorded in the database 130 (step 378). The reads may be temporarily recorded in the database 130 in a temporary database or table. In some embodiments, the raw read sequences may then be removed from the data repository 122 to save disk space. In some embodiments, the method 300 may include a step 332 of determining experiment information based on the descriptive data 330, for example, by the descriptive information determination module 116. In some embodiments, the descriptive data 330 may include but is not limited to organization or experimenter information (e.g., lab, etc.); related information (e.g., links to related pubmed publications); experiment information (e.g., type, experimental condition, date of experiment, etc.); dataset acquisition information (e.g., data source), organism information (e.g., e.g., organism and/or cell type); publication information (e.g., publication information, submission information, etc.); analysis information (e.g., analysis methods, summary metadata from analysis, etc.); provenance information (e.g., data creation timestamp, data injection timestamp, data analysis timestamp, etc.); as well as other metadata. The descriptive data may then be stored and indexed in the database 130.

The method 300 may include determining the experiment type from the descriptive data 330. In some embodiments, the type of experiment may include but is not limited to ChIP-Seq, RNA, BS-seq, TAB-seq, RIP-seq, CLIP-seq, SAGE-seq, among others, or a combination thereof. This may then be used to determine the quantitative information (step 326).

In some embodiments, the method 300 may include a step 326 of determining quantitative information for each group of one or more genes of the processed genomic data (e.g., one or more tracks) associated with the at least one dataset (determined from step 324), for example, by the quantitative information determination module 120. The quantitative information may relate to one or more quantitative measures of one or more biological properties associated with the processed genomic data. In some embodiments, the biological properties may include but are limited to protein-DNA interaction (ChIP-seq), strength gene expression (RNA-seq), DNA methylation (BS-seq), nucleosome position (MNase-seq), among others, or a combination thereof. In some embodiments, the quantitative information may be determined for a group of one or more genes in each track. The quantitative information may be based on a genomic coordinate system (or space) and/or experiment information (determined in step 332). In some embodiments, the quantitative information may be determined for at least the gene and region coordinate system.

In some embodiments, the quantitative information may include score information, rank information, among others, or a combination thereof. The score information may correspond to a normalized quantitative value corresponding to a (quantitative) measure of at least one biological property for each group of one or more genes in each track with respect to each coordinate system. In some embodiments, the measure may be based on the type of experiment and/or coordinate system. In some embodiments, the measure may be based on a test statistic, a p-value, or other statistical value with respect to differential expression, differential methylation (e.g., methylation levels), differential transcription factor binding, among others, or a combination thereof; a read count; among others, or a combination thereof. In some embodiments, the rank information, if determined, may relate to a quantitative value corresponding to a rank or percentile of the score information for each group of one or more genes in each track with respect to the coordinate system.

Figure 4A:
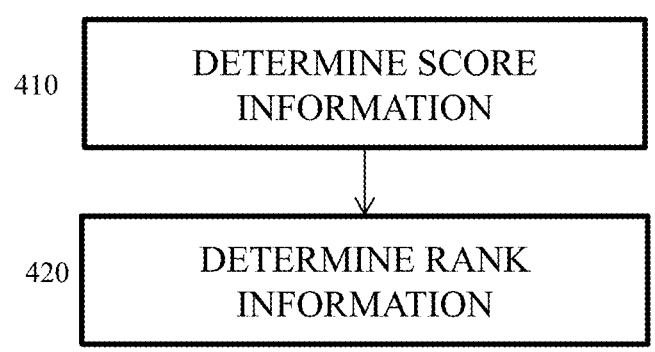
FIG. 4A shows a method of determining quantitative information for a gene coordinate system according to embodiments.

FIG. 4A shows a method 400 of determining quantitative information for gene coordinate system according to some embodiments. In some embodiments, the method 400 may include a step 410 of determining score information for each group of one or more genes in each track based on the coordinate system and/or experiment type.

In some embodiments, the score information for the gene coordinate system may be determined based on the promoter and/or coding region. The region may be dependent on the experiment type. For example, the score information for a track from a RNA experiment may be determined by enumerating the number of reads that are within the coding region of each gene, divided by the length of the coding region of the gene. For example, if the gene corresponds to si and the length of the coding region corresponds to di, the score information for each gene of that track can be s1/d1, s2/d2 . . . sN/dN. For example, the score information for a track from a ChIP-Seq experiment may be determined by enumerating the number of reads that are within the promoter region (e.g., upstream and downstream 500 bps around the transcription start site (TSS)) of each gene. For example, if the gene corresponds to si, the score information for this track can be s1, s2, . . . sN.

Figure 4B:
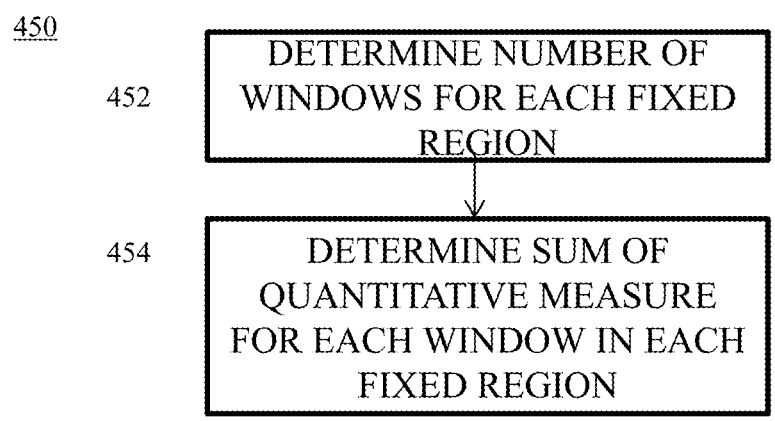
FIG. 4B shows a method of determining score information for a region coordinate system according to embodiments.

FIG. 4B shows a method 450 of determining score information for the region coordinate system. In some embodiments, the score information for the region coordinate system may be derived from calculating an empirical distribution of a measure for a plurality of different fixed region sizes of base pairs. The region sizes may be based on different fixed interval of different window sizes. The measure may be based on the type of experiment. In some embodiments, the measure may be based on a test statistic, a p-value, read count, result of a differential expression test, methylation levels, among others, or a combination thereof. In some embodiments, the region sizes may be increments of 500 base pairs (bp) 1,000 bp, 10,000 bp, and 100,000 bp, among others, or a combination thereof. For example, the regions sizes may include the following fixed region (i.e. window) sizes: 500 to 5,000 bp in increments of 500 (i.e., 500 bp, 1,000 bp, 1,500 bp, . . . 4,500 bp, and 5,000); 6,000 to 10,000 bp in increments of 1,000 bp (i.e., 6,000 bp, 7,000 bp . . . 10,000 bp); 10,000 to 100,000 bp in increments of 10,000 (i.e., 10,000 bp, 20,000 bp, . . . . 100,000 bp); and 100,000 to 1,000,000 bp in increments of 100,000 (i.e., 100,000 bp, 200,000 bp, . . . 1,000,000 bp). It will be understood that the region sizes may include different sized regions and interval increments; may include region sizes smaller than 500 bp; may include region sizes larger than 1,000,000; or a combination thereof.

It will be understood that the method 450 may be repeated for each fixed region (e.g., 500 bp, 1,000 bp, etc.). In some embodiments, the method 450 may include a step 450 of determining a number of non-overlapping windows ("L") for each fixed region ("n") across the genome. For example, the number "L" for each fixed region "n" may be determined by: $L=3.0e+09/n$. For example, if the fixed region (n) is 10,000 bp then L will be 300,000.

Next, the method 450 may include a step of determining a sum of the quantitative measure for each window in each fixed region. By way of example, the quantitative measure would be determined for each of the 300,000 windows for the 10,000 bp. For example, for ChIP-Seq experiment, the quantitative measure may be read counts.

Next, the method 400 may include a step 420 of determining rank information for each group of one or more genes in each track based on the coordinate system and/or experiment type.

Figure 5:
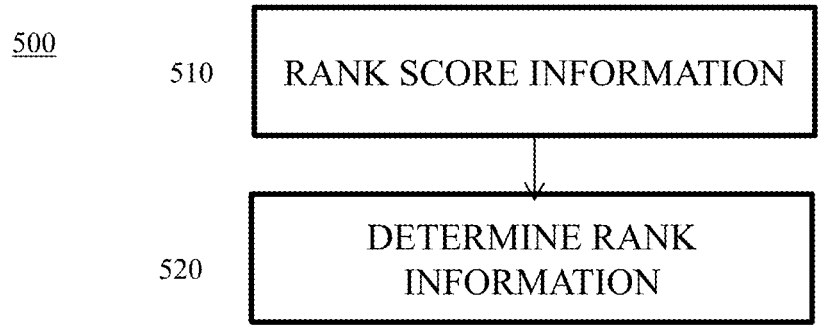
FIG. 5 shows a method of determining rank information according to embodiments.

FIG. 5 shows a method 500 of determining rank information according to embodiments. The method 500 may include a step 510 of ranking of the score information and converting that rank into percentiles.

In some embodiments, for the gene coordinate system, the score information may be ranked for the genes within a track from high to low such that the gene with highest score is ranked first. If there any genes with the same score, the ranks are treated as ties. Next, the rank information can be determined (step 520). In some embodiments, the rank information may be determined by dividing each rank by the largest rank so that the rank is transformed into a percentile. For example, for a gene ranked number 75 and the highest rank is 23580 in that track, the percentile for that gene would be $75/23580=0.32\%$. The rank information may then be stored relative to that gene.

In some embodiments, for the region coordinate system, the score information may be ranked and converted into percentiles. In this way, the score information (e.g., estimates of the percentile of the overall strength) in these regions may be relative to random regions in the genome of the same size.

For example, for a ChIP-Seq experiment, the empirical distribution of the test statistics resulting from the Chi-Square test may be determined for a plurality of region sizes (e.g., 500 bp, 1,000 bp, 1,500 bp, . . . 4,500 bp, and 5,000 bp). For a RNA-experiment, the empirical distribution of a p-value associated with the differential expression test may be determined for a plurality of region sizes (e.g., 500 bp, 1,000 bp, 1,500 bp, . . . 4,500 bp, and 5,000 bp). The rank information may then be stored relative to each window for each fixed interval (e.g., 10,000 bp).

After the quantitative information (e.g., score information and/or rank information) is determined (step 326), the quantitative information for each track may be stored in the database 130 according to the coordinate system. The descriptive data may also be stored in the database 130. In some embodiments, the quantitative information may be associated with the descriptive data by an index.

Figure 6:
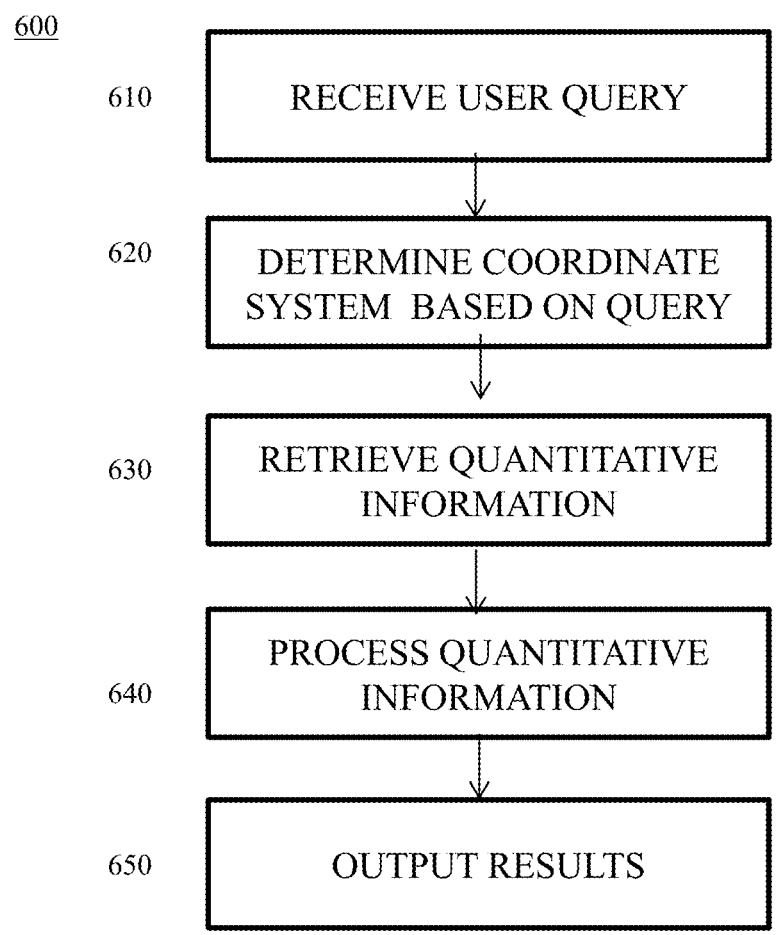
FIG. 6 shows a method of processing a user query to generate genomic information results according to embodiments.

FIG. 6 shows a method 600 of processing a user query, for example, by the genomic information query platform 140. In some embodiments, the method 600 may include a step 610 of receiving a user query for genomic information associated with a gene, genomic region, gene-set, among others, or a combination thereof.

In some embodiments, the method 600 may include a step 620 of processing the query to determine the coordinate system from which to retrieve quantitative information, for example, by the query processor 142. For example, if the query is for a single gene and/or gene-set, then the coordinate system may be the gene coordinate system. If the query is for a genomic region, then the coordinate system may be the genomic coordinate system.

In some embodiments, the method 600 may include a step 630 of retrieving the quantitative information associated with the query from the database 130, for example, by the quantitative information processor 144. For example, for a single gene query, the quantitative information associated with the gene may be retrieved for one or more genes. For a region query, the region size may be determined and the score information corresponding to that region size may be retrieved for one or more genes. For a gene-set query, the quantitative information for each gene in the set may be retrieved.

Figure 7:
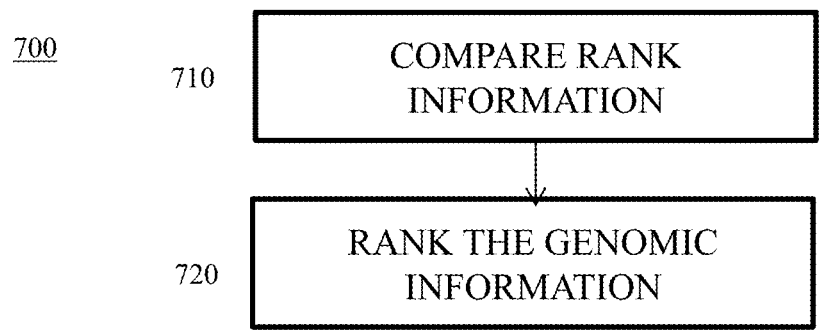
FIG. 7 shows a method of processing a query for a single gene according to embodiments.

The method 600 may include a step 640 of processing the retrieved quantitative information to determine the results, for example, by the quantitative information processor 144. The results may include a ranking of the genomic information related to the query based on the quantitative information. FIGS. 7-9 show examples of processing the quantitative information for a gene query, region query and gene-set query, respectively. In some embodiments, other methods may be used.

FIG. 7 shows a method 700 of processing quantitative information based on a gene query. In some embodiments, the method 700 may include a step 710 of comparing the rank information from the gene coordinate system (database 130) corresponding to the gene subject to the query to determine the highest rank information. The method may include a step 720 of ranking the track information according to the rank information, for example, from high to low. For example, the track information with the highest rank information may be ranked 1, the second highest rank information may be ranked 2, and etc.

Figure 8A:
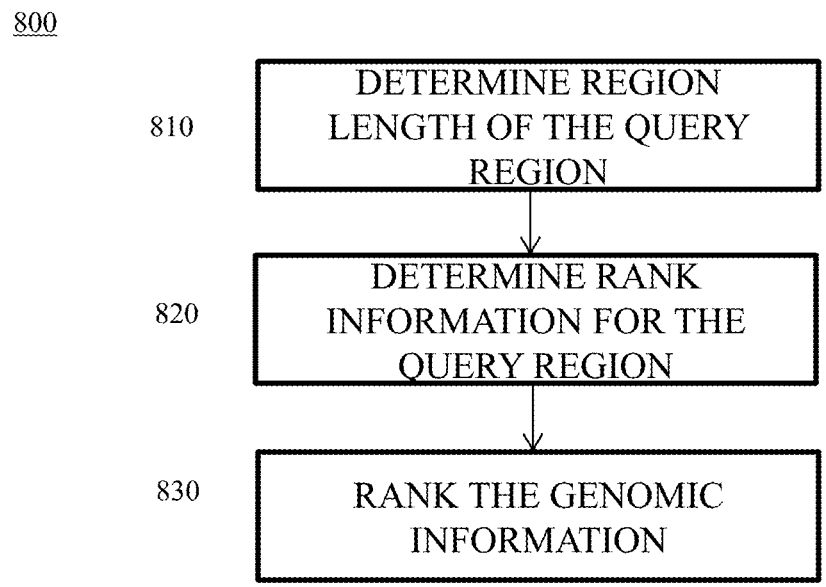
FIG. 8A shows a method of processing a query for a region according to embodiments.

FIG. 8A shows a method of processing quantitative information based on a genomic region query. In some embodiments, the method 800 may include a step 810 of determining a length of the query region. The method may include a step 820 of determining rank information for the query region based on the query length. For example, the rank information may be determined from a weighted average, interpolation and/or extrapolation.

Figure 8B:
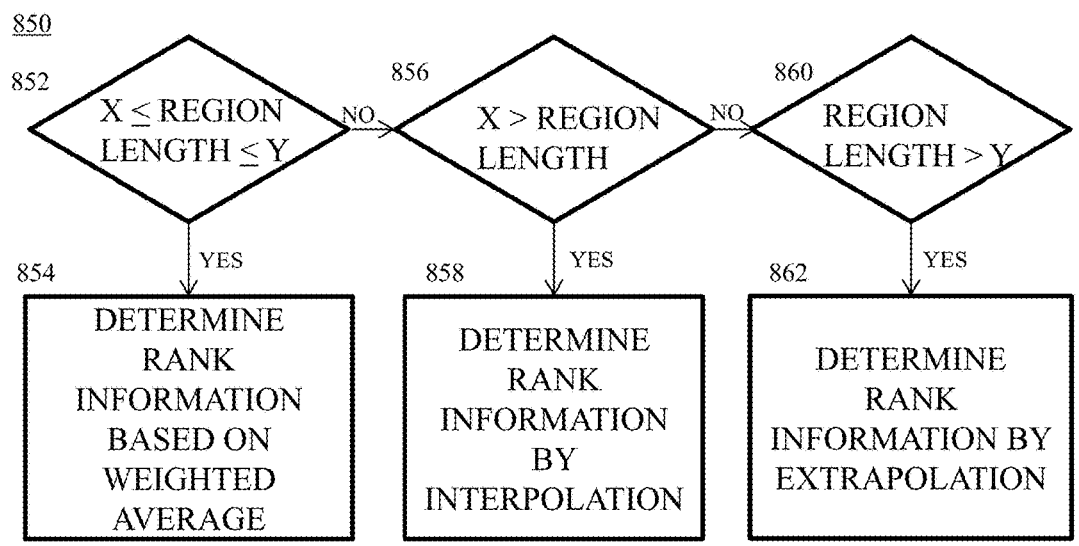
FIG. 8B shows a method of determining rank information for a query region according to embodiments.

FIG. 8B shows a method 850 of determining rank information for the genomic information based on the length of the region query according to embodiments. In some embodiments, the rank information may be determined by other methods.

As shown in FIG. 8B, the method 850 may include a step 852 of determining whether the region length is equal to and/or within threshold range X-Y. The threshold range may be based on the region intervals provided in the region database. In some embodiments, X may correspond to the smallest region size and Y may correspond to the largest region size. For example, in some embodiments, the 500 bp and Y may correspond to about 1,000,000 bp. In some embodiments, X and Y may correspond to different values. For example, X may correspond to 1,000 bp.

In some embodiments, if the length of the region query is within the range X-Y (YES at step 852), then the rank information may be determined by calculating the weighted average based on the closet neighboring interval(s) (step 854). If the length of the region query is less than X (NO at step 852 and YES at 856), then the rank information may be determined by interpolation (step 858). If the length of the region is greater than Y (NO at step 856 and YES at step 860), then the rank information may be determined by extrapolation (step 862).

In some embodiments, the method 800 may include a step 830 of ranking the rank information according to the determined rank information, for example, from high to low, like the gene query.

Figure 9A:
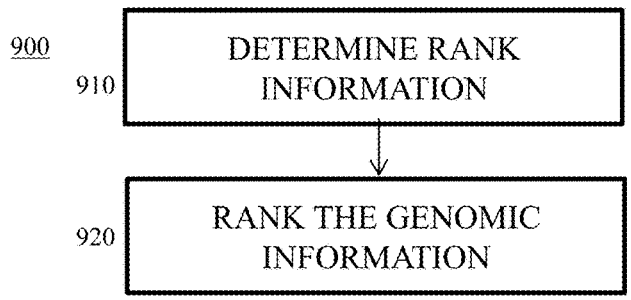
FIG. 9A shows a method of processing a query for a gene-set according to embodiments.

FIG. 9A shows a method of processing quantitative information based on a gene-set query. In some embodiments, the method 900 may include a step 910 of determining rank information within each track using the score information from the gene coordinate system (database 130) based on the number of sets of gene in the query. For example, the rank information may be determined using sum distribution and/or central limit theorem.

Figure 9B:
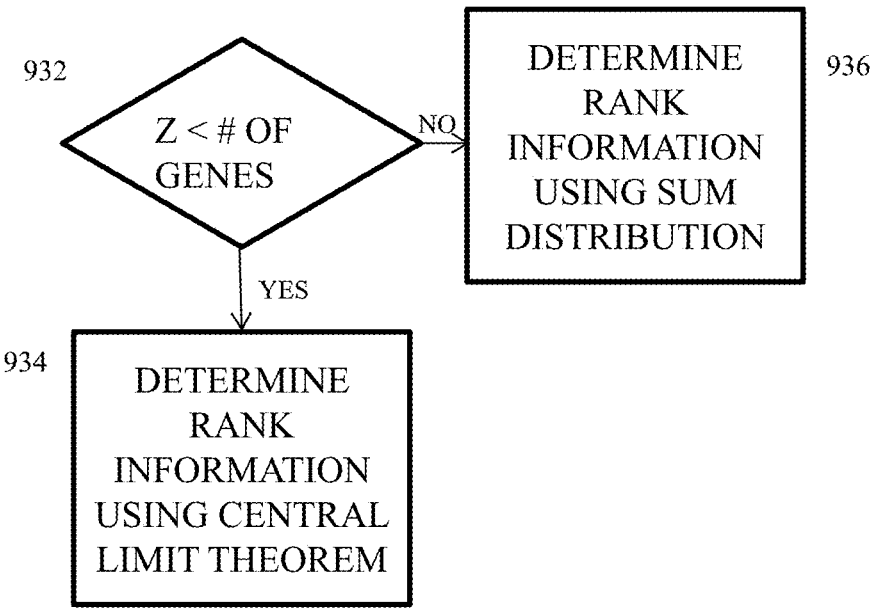
FIG. 9B shows a method of determining rank information for a gene-set query according to embodiments.

FIG. 9B shows a method 930 of determining rank information for the genomic information based on number of genes in the gene set query according to embodiments. In some embodiments, the rank information may be determined by other methods.

As shown in FIG. 9B, the method 930 may include a step 932 of determining whether the number of genes in the gene set query is greater than a threshold value (Z). In some embodiments, Z may correspond to 10. In other embodiments, Z may be greater and/or lesser than 10. In some embodiments, if the number of genes in the gene set query is greater than Z (YES at step 932), then the rank information may be determined by sum distribution (step 934). If the number of genes in the gene set query is less than Z (NO at step 932), then the rank information may be determined by central limit theorem (step 858).

Next, the method 900 may include a step 920 of ranking the rank information from high to low.

Next, the method 600 may include a step of 650 of outputting results, for example, by the genomic information results generator 146. In some embodiments, the outputting may include displaying, printing, storing, and/or transmitting the results. The results may include a ranking of the genomic information based on the quantitative information. In some embodiments, the results may include a ranking of datasets according to the ranking of the quantitative information and the corresponding descriptive data. The results may include a link for each dataset to one or more sites for downloading and/or viewing the genomic data associated with the dataset(s). In this way, a user can select a dataset(s), for example, for downloading the dataset, viewing the dataset using the UCSC Genome browser, viewing the metadata, and/or access the originating site to download the genomic data.

Figure 10A:
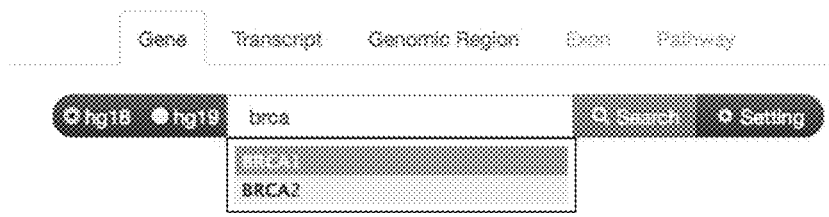
FIGS. 10A-10C show examples of user interfaces according to embodiments.
Figures 10B, 10C:
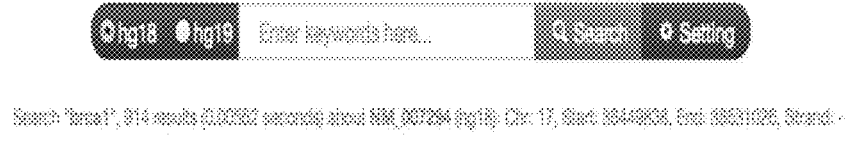

FIGS. 10A-10C show examples of a user interface (user query module) according to embodiments. FIGS. 10A-10C shows an example of a user interface for receiving user (single gene) query and outputting results for genomic information associated with the BRCA1 gene. FIG. 10A shows an example a user interface of the genomic information query platform 140. In FIG. 10A, a user queries for genomic information associated with BRCA1.

FIG. 10B shows an example of a user interface outputting results of genomic information associated with BRCA1 gene from the database 130. As shown in FIG. 10B, the results may include a ranking of the genomic information. This ranking is based on the quantitative information (determined by the platform 110) associated with each dataset and stored in the database 130. As shown in FIG. 10C, the genomic information includes the descriptive data associated with each dataset.

FIG. 10C shows an example of further information provided by the platform 140 utilizing the quantitative information determined by the platform 110. FIG. 10C shows the results when the accession identifier, (e.g. NM_007294) is clicked by a user. In some embodiments, the additional results may include the one or more ranked cell lines associated with the gene query (e.g., BRCA1).

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

In some embodiments, the disclosed methods (e.g., FIGS. 3-9) may be implemented using software applications that are stored in a memory and executed by a processor (e.g., CPU) provided on the system 100. In some embodiments, the disclosed methods may be implanted using software applications that are stored in memories and executed by CPUs distributed across the system 100. As such, any of the systems and/or modules of the system 100 may be a general purpose computer system, such as system 200, that becomes a specific purpose computer system when executing the routine of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 2.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method of generating comparable genomic information from a plurality of raw genomic datasets, comprising:
   processing at least one dataset that includes raw genomic data and descriptive data obtained from a data repository to generate one or more groups of one or more genes from the raw genomic data and to extract experiment data from the descriptive data for the at least one dataset;
   generating quantitative information for each group of one or more genes of the at least one dataset based on the experiment data and/or one or more genomic coordinate systems for each of the one or more genomic coordinate systems;
   wherein the one or more genomic coordinate systems includes a genomic region coordinate system and a gene coordinate system;
   wherein each coordinate in the gene coordinate system relate to individual genes and each coordinate in genomic region coordinate system relates to a fixed interval of base pairs; and
   wherein the generating quantitative information for each group of one or more genes of the at least one dataset includes:
      determining one or more quantitative measures of one or more biological properties for each group of one or more genes of the at least one dataset based on the experiment data and/or one or more genomic coordinate systems for each of the one or more genomic coordinate systems;
      generating a score information based on the one or more quantitative measures of one or more biological properties for each group of genes with respect to each genomic coordinate system and the at least one dataset, the score information for each group of genes corresponding to a normalized value corresponding to the one or more quantitative measures of one or more biological properties for each group of one or more genes with respect to each coordinate system and the at least one dataset; and
      generating a rank information from the score information for each group of one or more genes with respect to the coordinate system and the at least one dataset, the rank information corresponding to a ranking of the score information for each group of one or more genes within each dataset and coordinate system; and
   storing the quantitative information for each group of the one or more genes of the at least one dataset in at least one database, wherein the quantitative information are stored with respect each coordinate system separately in the at least one database.

2. The method according to claim 1, wherein the one or more quantitative measures is based on experiment type included in the experiment data.

3. The method according to claim 2, wherein:
   the score information for the gene coordinate system is determined based on a region, the region corresponding to promoter and/or coding region; and
   the region is based on the experiment type included in the experiment data.

4. The method according to claim 3, wherein:
when the region corresponds to the coding region, the score information for each group of genes is generated by enumerating a number of reads that are within the coding region of each gene group dividing by a length of the coding region of the each gene group; and
when the region corresponding to the promoter region, the score information for each group of genes is generated by enumerating a number of reads that are within the promoter region of each gene group.

5. The method according to claim 2, wherein the one or more quantitative measures includes a test statistic and/or a p-value with respect to differential expression, differential methylation, and/or differential transcription factor binding; and/or a read count.

6. The method according to claim 5, wherein:
when the experiment type is a RNA-experiment, the quantitative measure for each group of genes corresponds to the p-value with respect to differential expression; and
when the experiment type is a ChIP-Seq experiment, the quantitative measure for each group of genes corresponds to a test statistic p-value with respect to differential expression.

7. The method according to claim 1, wherein the processing the at least one dataset that includes raw genomic data to generate one or more groups of one or more genes from the raw genomic data includes mapping the raw genomic data to a reference genome.

8. A system for generating comparable genomic information from a plurality of raw genomic datasets, the system comprising:
at least one processor; and
a memory, wherein the processor is configured to cause:
processing at least one dataset that includes raw genomic data and descriptive data obtained from a data repository to generate one or more groups of one or more genes from the raw genomic data and to extract experiment data from the descriptive data for the at least one dataset;
generating quantitative information for each group of one or more genes of the at least one dataset based on the experiment data and/or one or more genomic coordinate systems for each of the one or more genomic coordinate systems;
wherein the one or more genomic coordinate systems includes a genomic region coordinate system and a gene coordinate system;
wherein each coordinate in the gene coordinate system relate to individual genes and each coordinate in genomic region coordinate system relates to a fixed interval of base pairs; and
wherein the generating quantitative information for each group of one or more genes of the at least one dataset includes:
determining one or more quantitative measures of one or more biological properties for each group of one or more genes of the at least one dataset based on the experiment data and/or one or more genomic coordinate systems for each of the one or more genomic coordinate systems;
generating a score information based on the one or more quantitative measures of one or more biological properties for each group of genes with respect to each genomic coordinate system and the at least one dataset, the score information for each group of genes corresponding to a normalized value corresponding to the one or more quantitative measures of one or more biological properties for each group of one or more genes with respect to each coordinate system and the at least one dataset; and
generating a rank information from the score information for each group of one or more genes with respect to the coordinate system and the at least one dataset, the rank information corresponding to a ranking of the score information for each group of one or more genes within each dataset and coordinate system; and
storing the quantitative information for each group of the one or more genes of the at least one dataset in at least one database, wherein the quantitative information are stored with respect each coordinate system separately in the at least one database.

9. The system according to claim 8, wherein the one or more quantitative measures is based on experiment type included in the experiment data.

10. The system according to claim 9, wherein the one or more quantitative measures includes a test statistic and/or a p-value with respect to differential expression, differential methylation, and/or differential transcription factor binding; and/or a read count.

11. The method according to claim 10, wherein:
when the experiment type is a RNA-experiment, the quantitative measure for each group of genes corresponds to the p-value with respect to differential expression; and
when the experiment type is a ChIP-Seq experiment, the quantitative measure for each group of genes corresponds to a test statistic p-value with respect to differential expression.

12. The system according to claim 9, wherein:
the score information for the gene coordinate system is determined based on a region, the region corresponding to promoter and/or coding region; and
the region is based on the experiment type included in the experiment data.

13. The method according to claim 12, wherein:
when the region corresponds to the coding region, the score information for each group of genes is generated by enumerating a number of reads that are within the coding region of each gene group dividing by a length of the coding region of the each gene group; and
when the region corresponding to the promoter region, the score information for each group of genes is generated by enumerating a number of reads that are within the promoter region of each gene group.

14. The method according to claim 8, wherein the processing the at least one dataset that includes raw genomic data to generate one or more groups of one or more genes from the raw genomic data includes mapping the raw genomic data to a reference genome.

15. A method of ranking of genomic information based on a query for genomic information, the method comprising:
providing a plurality of quantitative databases that stores genomic information based on one or more genomic coordinate systems; the plurality of quantitative databases including a quantitative database based on a gene-based coordinate system and a quantitative database based on a genomic region coordinate system, each quantitative database including quantitative information for each coordinate corresponding to the coordinate system, each coordinate for the gene-based coordinate system corresponding to a gene and each coordinate for the genomic region coordinate system corresponding to a fixed interval of base pairs;

processing a query for genomic information, the query corresponding to a query for a single gene, a query for a set of two or more genes, and/or a query for a genomic region of one or more genes;

selecting a quantitative database from the plurality of quantitative databases based on a genomic coordinate system associated with the query, the quantitative database based on the gene-based coordinate system is selected for the query for the single gene and/or the query for a set of two or more genes; and the quantitative database based on the genomic region coordinate system is selected for the query for the genomic region of one or more genes;

retrieving the quantitative information associated with the genomic information from the selected quantitative database based on the query, the quantitative information corresponding to one or more quantitative measures of one or more biological properties associated with one or more processed genomic datasets obtained from a data repository;

processing the quantitative information to determine a ranking of the genomic information based on the quantitative information; and generating results, the results including the ranking of the genomic information based on the quantitative information; the genomic information including genomic data and descriptive data.

16. The method according to claim 15, wherein the one or more quantitative measures is based on experiment type associated with each genomic dataset included in the plurality of quantitative databases.

17. The method according to claim 16, wherein:

the score information for the gene coordinate system is determined based on a region, the region corresponding to promoter and/or coding region; and the region is based on the experiment type included in the experiment data.

18. The system according to claim 16, wherein the one or more quantitative measures includes a test statistic and/or a p-value with respect to differential expression, differential methylation, and/or differential transcription factor binding; and/or a read count.

* * * * *